United States Patent
Zhang et al.

(10) Patent No.: US 7,142,693 B2
(45) Date of Patent: Nov. 28, 2006

(54) METHOD OF GRADING SAMPLE

(75) Inventors: Yupeng Zhang, Knoxville, TN (US); Christopher K. Shofner, Knoxville, TN (US); Frederick M. Shofner, Knoxville, TN (US)

(73) Assignee: Shofner Engineering Associates, Inc., Knoxville, TN (US)

( * ) Notice: Subject to any disclaimer, the term of this patent is extended or adjusted under 35 U.S.C. 154(b) by 531 days.

(21) Appl. No.: 10/192,143

(22) Filed: Jul. 10, 2002

(65) Prior Publication Data

US 2003/0059090 A1  Mar. 27, 2003

Related U.S. Application Data

(60) Provisional application No. 60/304,653, filed on Jul. 11, 2001.

(51) Int. Cl.
*G06K 9/00* (2006.01)

(52) U.S. Cl. .................................................. 382/100

(58) Field of Classification Search ................ 382/110, 382/111; 356/238.1
See application file for complete search history.

(56) References Cited

U.S. PATENT DOCUMENTS

| | | | |
|---|---|---|---|
| 5,125,279 A * | 6/1992 | Anthony et al. ............... 73/866 |
| 5,130,559 A * | 7/1992 | Leifeld et al. ......... 250/559.11 |
| 5,539,515 A * | 7/1996 | Shofner et al. .......... 356/238.3 |
| 6,567,538 B1 * | 5/2003 | Pelletier ..................... 382/111 |
| 6,621,915 B1 * | 9/2003 | Chen et al. ................. 382/111 |

OTHER PUBLICATIONS

Michael A. Lieberman, Evaluation of Learning vector Quantization to classify cotton Trash, Mar. 1997, Opt. Engineering, 36(3) 914-921.*

* cited by examiner

*Primary Examiner*—Samir Ahmed
*Assistant Examiner*—ONeal R. Mistry
(74) *Attorney, Agent, or Firm*—Pitts & Brittian, P.C.

(57) ABSTRACT

Method of grading a sample. An input color image of the sample, such as a sample of raw cotton, is obtained by a scanning technique. This image is first analyzed by an image segmentation module and a binary image where pixels of a first characteristic are marked as 0 (e.g. cotton lint) and non-lint pixels are marked as 1. In a following particle recognition module, the adjacent non-lint pixels are grouped together as particles, and the color, size, shape and edge strength for each particle are computed. The particle descriptions are analyzed and each particle is assigned a trash type, i.e. leaf, bark, grass, pepper trash or shadow. The data of leaf and pepper trash are analyzed by a leaf grading module and leaf grade is reported. The data of bark/grass are analyzed by a bark/grass grading module and the bark/grass grade is reported.

14 Claims, 19 Drawing Sheets

Marked Image: Red - Leaf; Green - Bark/Grass, Black - Pepper Trash, Gray - Shadow

|  | $j-1$ | $j$ | $j+1$ |
|---|---|---|---|
| $i-1$ | 0 | 1 | 0 |
| $i$ | 1 | 1 | 0 |
| $i+1$ | 1 | 1 | 1 |

*Figure 13* ith Layer, jth neuron structure
(n inputs, 1 output)

METHOD OF GRADING SAMPLE

CROSS-REFERENCE TO RELATED APPLICATIONS

RELATED APPLICATIONS

This application is a non-provisional application and claims priority based on U.S. provisional patent application Ser. No. 60/304,653 filed Jul. 11, 2001.

FIELD OF INVENTION

This application relates to non-human classification of bulk raw cotton.

BACKGROUND

Cotton trash is any non-lint material in the cotton. Examples of cotton trash are leaf, bark, grass and small foreign particles known as pepper trash. The amount of trash in cotton bales is a crucial factor in determining the market value of the cotton. The value used in determining cotton market value is classer's Leaf Grade and Bark/Grass Grade. The kind of trash and an indication of the amount (the Leaf Grade "1" through "7" and the Bark/Grass Grade "0", "1" or "2") are visually estimated by a human classer. Classer determination for leaf grade and bark/grass grade has been used for many decades and is still part of the official U.S. Department of Agriculture (USDA) cotton classification. No automatic system is known to be used to determine leaf grade and bark/grass grade currently.

Although the USDA provides High Volume Instrument (HVI) trash measurement, the correlation between HVI trash and classer's Leaf Grade is very low, and it is impossible to get Bark/Grass Grade from the HVI trash measurement. HVI trash is a measure of the amount of non-lint materials in the cotton, such as leaf, bark and grass. HVI trash measurement systems analyze the gray-scale images of a cotton sample surface using a fixed intensity threshold to identify pixels in cotton image as "lint" or "non-lint". The amount of trash is then quantified as the percentage of the surface area occupied by non-lint pixels. While this method performs well if the cotton is bright white in color, the trash particles are always much darker than the lint, and the image light source does not degrade with use, these assumptions are often not satisfied in practice. Cotton colors range from bright white to dark yellow, non-lint material varies in darkness, and light sources degrade with use. Thus, it is not possible to assign a single threshold that is able to accurately discriminate between lint and non-lint material under all commonly encountered conditions. On the other hand, since all pixels that are darker than a certain threshold are considered as trash, the HVI trash system can not distinguish leaf, bark and grass, even shadows. That makes HVI trash system can not make good leaf grade and is impossible to make bark/grass grade.

The major advantage of human classing of cotton lies in the capability of a human being learning, organizing and accumulating knowledge. An experienced human classer can do a better job of categorizing and grading the cotton than any heretofore known computer system. However, the disadvantages are rather obvious. It is much more expensive to train and maintain a human classing system than a computer classing system. The reproducibility between two different individuals is lower compared to reproducibility between multiple computer systems. Moreover, a human classer can not quickly make accurate measurement of such as things as particle count, percentage area occupied by trash and average size of the trash particle. Thus, industry demands an automatic, accurate and reliable trash measurement system to replace the traditional human classing system for cotton.

Many attempts have been made to track a human classer's leaf grade based on percentage of surface area occupied by trash particles or count of trash particles, but all have failed. A human classer is trained using USDA leaf standard and a large number of cotton samples with known leaf and bark/grass grade. An experienced human classer forms a visual image of a cotton sample and usually determines leaf and bark/grass grade within few seconds for each sample. They never actually count the particles in the cotton sample or measure the size of the particles. What they do is first to categorize the content in the cotton sample to several categories and estimate the amount of each category based upon their image of the sample as compared to their "learned" standards. Second, they mentally process the information and make a leaf and bark/grass grade according to the knowledge that they learned through training and experience.

A successful non-human trash measurement system desirably would be able to emulate the human classer's system. First, the system must have the ability to categorize the content of the cotton image. There are lint, leaf, bark, grass, and shadows in a sample image. The system must be able to categorize the pixels in the cotton image into these categories and compute the amount of each category.

Second, the system must have the ability to implement and maintain a mathematical model that is able to learn the knowledge and process the multiple dimensional information non-linearly.

Image segmentation is the process of dividing images into sets of coherent regions or objects. It is one of the most difficult tasks in computer vision. It plays a critical role in object recognition of natural images. Unsupervised classification, or clustering, represents one promising approach for solving the image segmentation problem in typical application environments. The K-Means and Bayesian Learning algorithm are two well-known unsupervised classification methods. The K-Means approach is computationally efficient but assumes imaging conditions which are unrealistic in many practical applications. While the Bayesian learning technique always produces a theoretically optimal segmentation result, the large computational burden it requires is often unacceptable for many industrial tasks. A novel clustering algorithm, called Bayesian Weighted K-Means, is developed to divide the cotton image into lint and non-lint regions in trash measurement system. Through simplification of the Bayesian learning approach's decision-making process using cluster weights, the new technique is able to provide approximately optimal segmentation results while maintaining the computational efficiency generally associated with the K-Means algorithm.

Artificial Neural Network is an information-processing paradigm. It is based on the processing/memory abstraction of human information processing. Artificial neural network is composed of a large number of highly interconnected neurons that are connected with weighted connections. Each neuron is a mathematical model that emulates some of the features of biological neuron such as biological learning. Artificial Neural Network iteratively adjusts the connection weights based on a training set to learn the knowledge that is necessary to solve specific problems. The high non-linear structure and the capability of learning make the Artificial Neural Network well suit the problem that people are good at solving, but for which traditional methods are not. Artificial Neural Networks are used in trash measurement system to solve the leaf and bark/grass grading problems.

SUMMARY OF THE INVENTION

It is an objective of the present invention to provide an automatic, fast, reliable and robust color image-based trash measurement system which is able to replace the traditional human classing system with is particularly useful in grading of cotton. The present trash measurement system analyzes the high resolution, digital color image of a cotton sample accurately and precisely. Selected physical properties of the sample are computed employing the data obtained through the analysis of the digital color image. For example, the present system will provide identification of the kind of trash in the sample, and measurements of percentage of surface area occupied by trash particles in a cotton sample, along with particle counts and average particle size for each kind of trash particle. The system will identify and quantify Leaf Grade and Bark/Grass Grade, which are highly correlated with leaf grade standard. It will also provide a visible marked cotton image where different kinds of particles are highlighted with different colors ("marked"). The detail information of each trash particle including color, size, shape, type will be output in a particle analysis report. The data collected is employed to provide an output of the class of the cotton of the sample.

An input color image of a cotton sample is obtained by a scanning technique. This image is first analyzed by an image segmentation module and a binary image where lint pixels are marked as 0 and non-lint pixels are marked as 1. In a following particle recognition module, the adjacent non-lint pixels are grouped together as particles, and the color, size, shape and edge strength for each particle are computed. These particle descriptions are analyzed and each particle is assigned a trash type: leaf, bark, grass, pepper trash or shadow. The data of leaf and pepper trash are analyzed by a leaf grading module, and leaf grade is reported. The data of bark/grass are analyzed by a bark/grass grading module and the bark/grass grade is reported. Samples with known leaf grade and bark/grass grade will be used to train the system. The parameters or the structure of the mathematical model will be adjusted based on the training data to store the knowledge. The core technology used in this step is Artificial Neural Network.

BRIEF DESCRIPTION OF THE FIGURES

FIG. 13 illustrates the 8-connectivity concept as employed in the present invention;

DETAILED DESCRIPTION OF THE INVENTION

Figure 4:
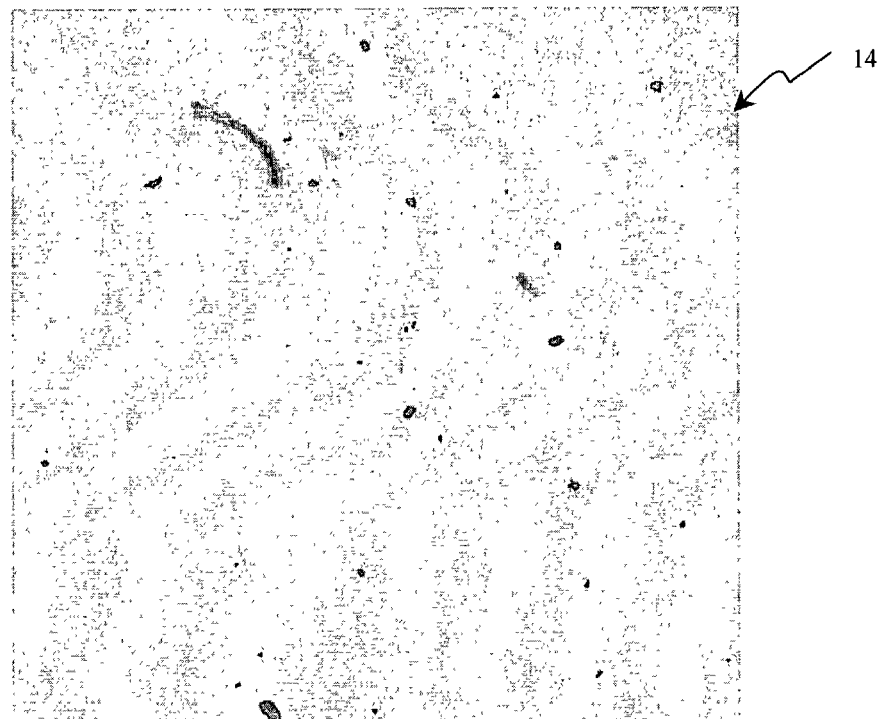
FIG. 4 is an example of typical output results obtained through the use of the present system, including marked image, Leaf Grade, Bark/Grass Grade, nine measurements and particle analysis report from a typical cotton sample.

Referring to Figures land 2, one embodiment of the present invention includes an input 12 comprising a high resolution, digital color image of a cotton sample 14 such as shown in FIGS. 3(a)–3(d). The system 18 conducts analysis measurements 16 of the input image and outputs Leaf Grade 20, Bark/Grass Grade 22, marked image 24, particle analysis report 26 and nine measurements as depicted in FIG. 4 and Table A.

TABLE A

Leaf Grade 2.1
Bark/Grass Grade 1

| Measurements | Leaf | Pepper Trash | Bark/Grass |
|---|---|---|---|
| % Area | 0.215 | 0.052 | 0.279 |
| Count/Inch$^2$ | 1.451 | 2.790 | 0.223 |
| Mean Size (μm) | 977.158 | 345.374 | 2838.5 |

Particle Analysis Report (Partial)
(Type: 1-Leaf, 2-Bark/Grass, 7-PepperTrash)

| LG | Size | CIEL | CIEa | CIEb | Length | Width | Edge | Type |
|---|---|---|---|---|---|---|---|---|
| 2 | 911.9 | 68.7 | −3.9 | 12.9 | 617.7 | 322.4 | 31.1 | 1 |
| 2 | 987.4 | 69.6 | −3.5 | 9.6 | 662.9 | 477.6 | 24.4 | 1 |
| 2 | 478.9 | 68.9 | −3.6 | 10.9 | 0 | 0 | 40.3 | 7 |
| 2 | 3729.2 | 64.9 | −2.5 | 9.7 | 86863.3 | 3069.4 | 42.2 | 2 |
| 2 | 293.3 | 66.2 | −2.5 | 8.9 | 0 | 0 | 47.5 | 7 |

TABLE A-continued

Leaf Grade 2.1
Bark/Grass Grade 1

| 2 | 535.5 | 64.9 | 5  | 27.7 | 343.4 | 96.9 | 55.7 | 1 |
|---|-------|------|----|------|-------|------|------|---|
| 2 | 1016  | 66.5 | -2 | 13   | 1559  | 219  | 43.8 | 1 |

In a preferred embodiment, the present system includes at least four major modules, namely: Image Segmentation 30, Particle Recognition 32, Leaf Grading 34 and Bark/grass Grading 36.

A. Image Segmentation Module

Figure 5:
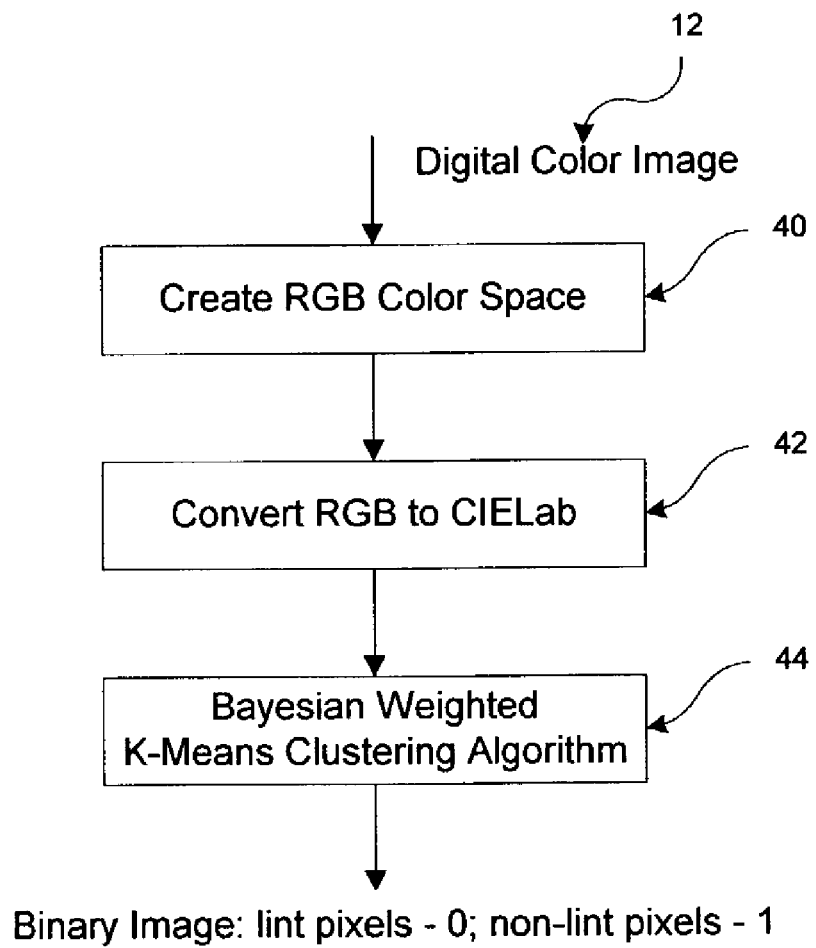
FIG. 5 is the generalized flow diagram of one embodiment of an image segmentation module as employed in the present invention.

FIG. 5 depicts a generalized flow diagram of one embodiment of a Image Segmentation module 30 of the present invention. The objective of the module is to divide the digital color image 12 of a cotton sample, for example, into lint regions and non-lint regions. The output of the module is a binary image in which lint pixels are "marked" as 0 and non-lint pixels are "marked" as 1.

Figure 6:
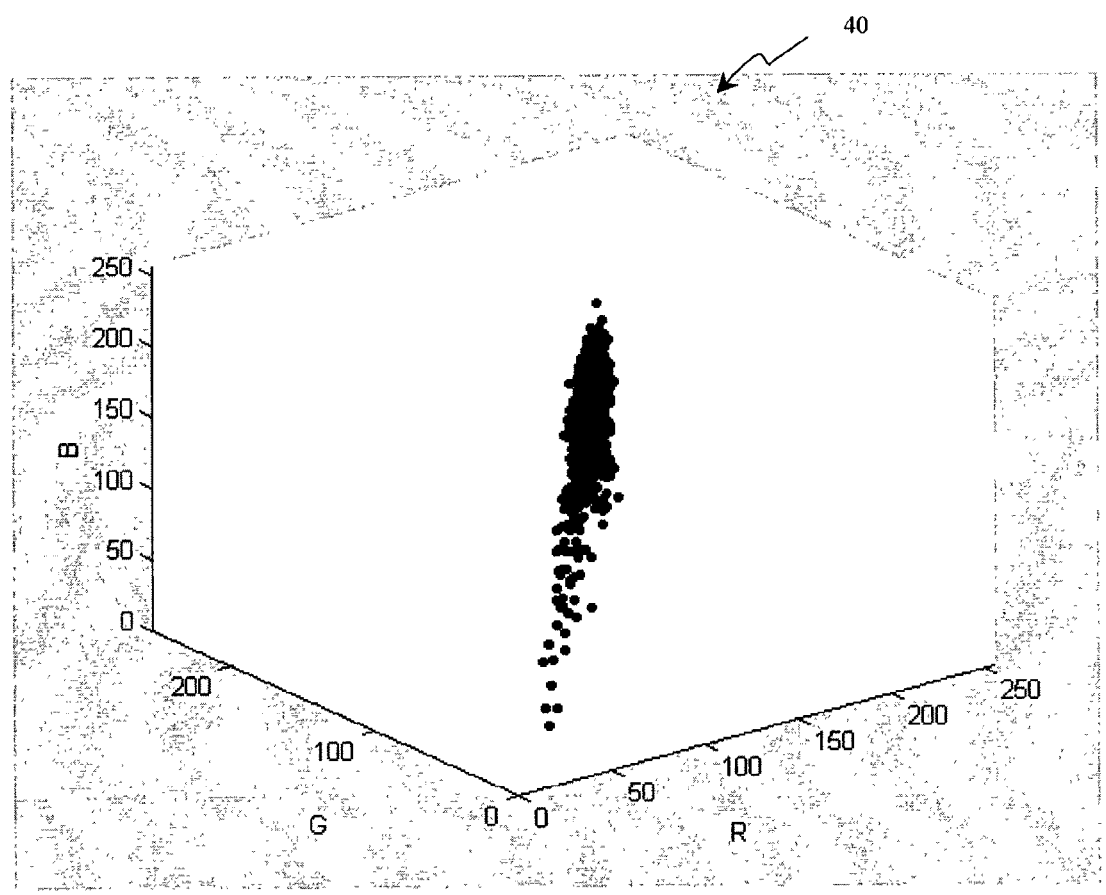
FIG. 6 depicts in black and white the RGB color space of a typical cotton sample.
Figure 7:
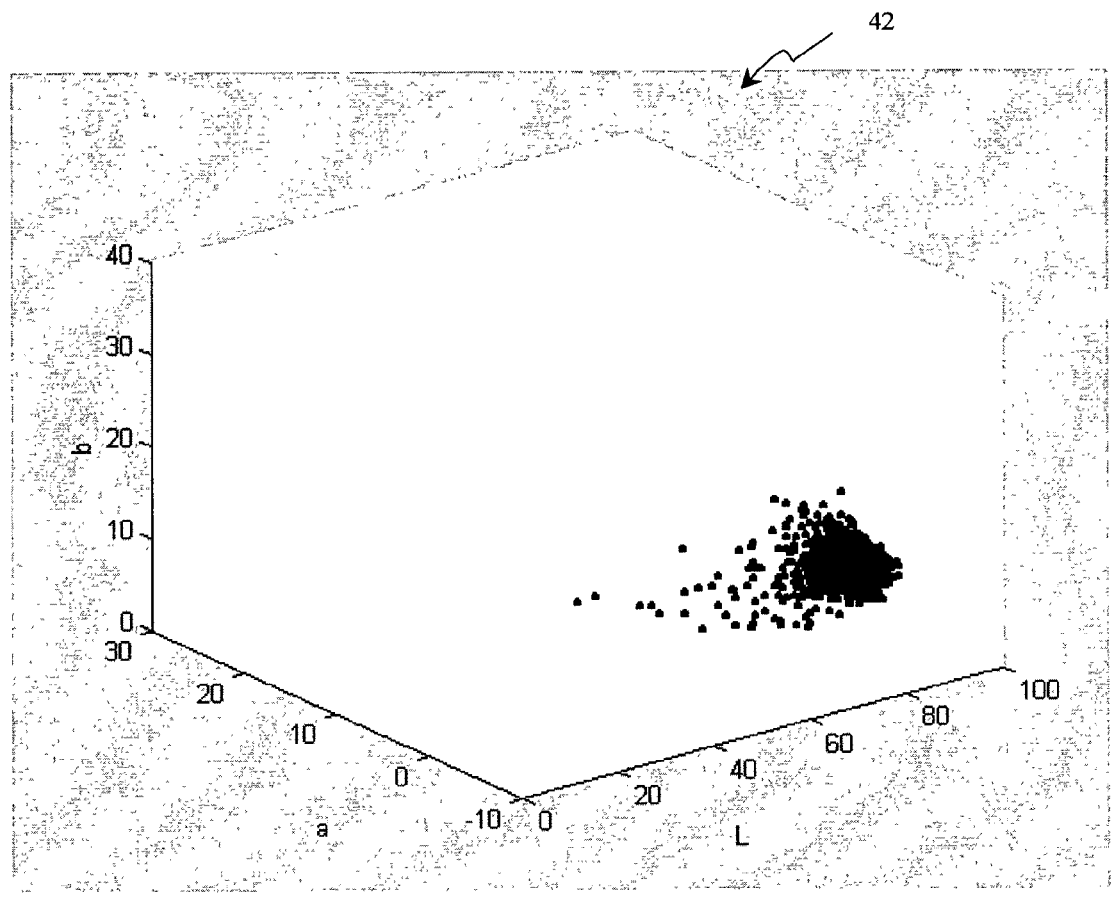
FIG. 7 depicts in black and white the CIELAB color space of the cotton sample depicted in FIG. 6.
Figure 8:
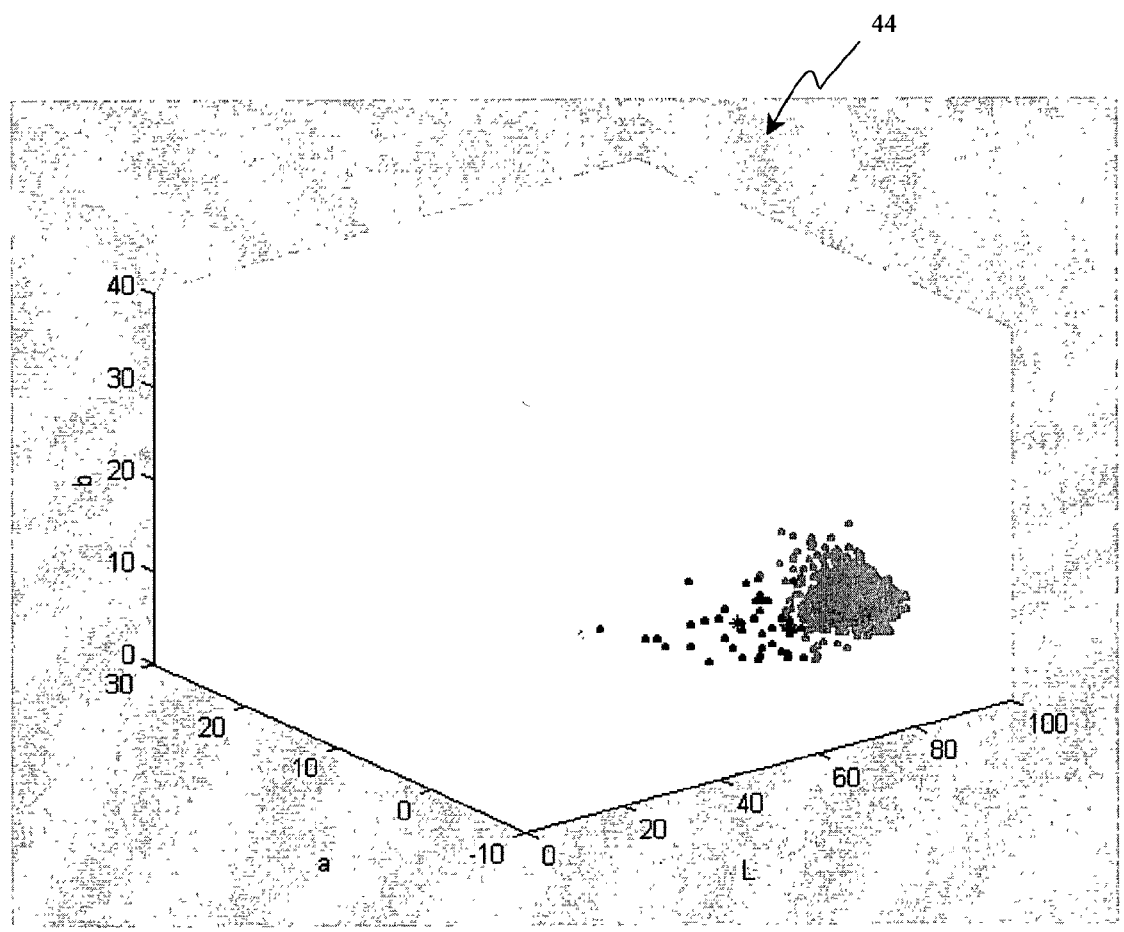
FIG. 8 depicts in black and white the classified CIELAB color space of the cotton sample depicted in FIG. 6.
Figure 9:
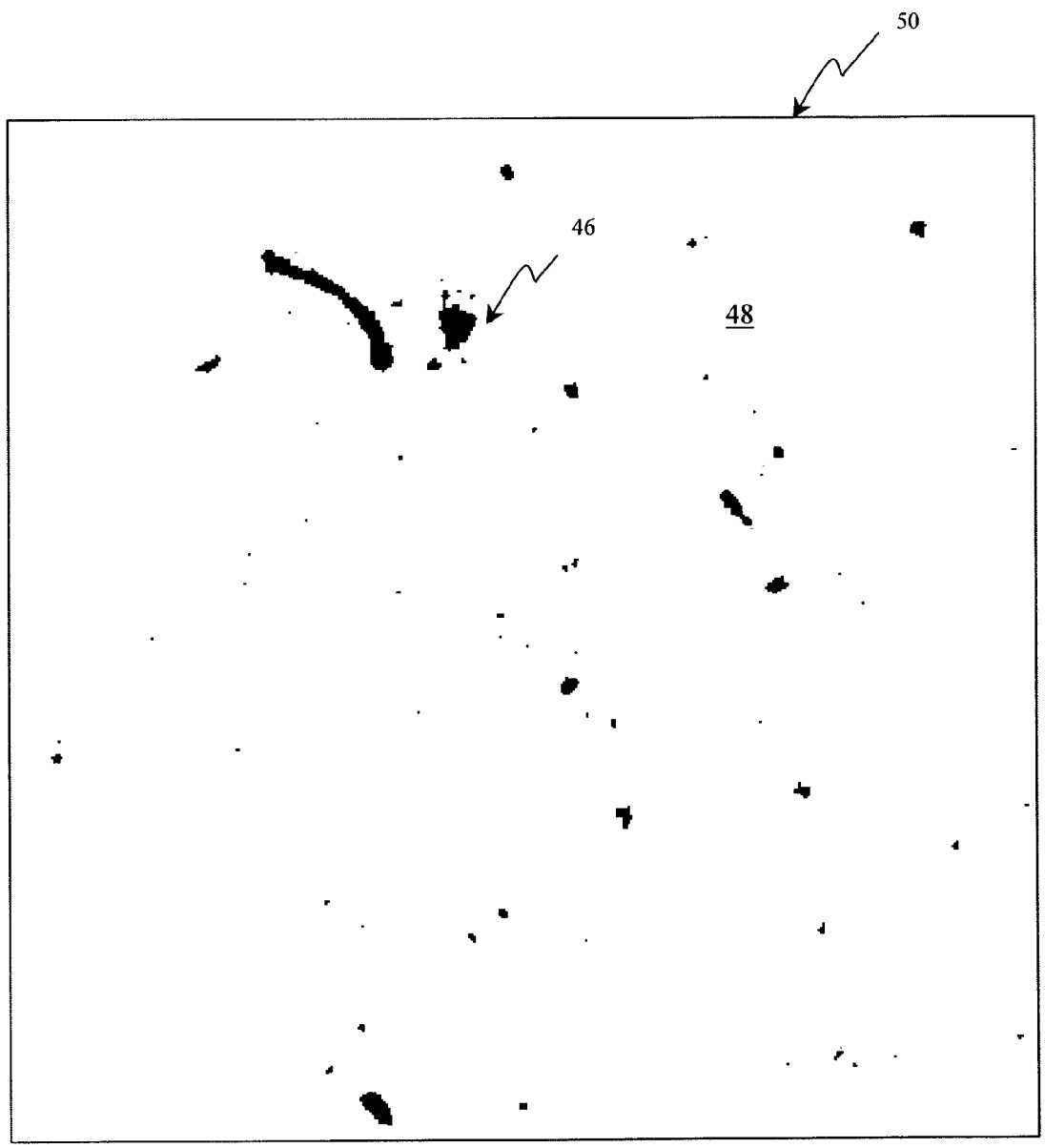
FIG. 9 depicts in black and white one example of binary image produced by the image segmentation module of the present invention.

In one embodiment three steps are employed to identify the non-lint material in the cotton image. First, a RGB color space 40, as shown in FIG. 6, is created from the input color image. The high-resolution input image preferably has at least 1.3 million pixels, hence it is time consuming to process. Since the cotton image is mostly white, yellow or gray, a large number of the pixels are substantially the same color, in other words, RGB (Red, Green, and Blue) value. Following this step, the frequency of appearance of color (R, G, B) is recorded in the related (R, G, B) coordinate of color space and the size of data set is reduced to one percent of the original data set. Second, the RGB color space is converted to the perceptually uniform CIELAB color space 42, as shown in FIG. 7. In the CIELAB model, the color differences, which are perceived by human eyes, correspond to distances measured calorimetrically. Third, a novel technique defined as Bayesian Weighted K-Means Clustering Algorithm 44 is used to classify the data points in the CIELAB color space into two clusters: lint 46 and non-lint 48 as shown in FIG. 8. FIG. 9 depicts the output binary image 50 where lint pixels 46 (typical) are marked as 0 (white) and non-lint pixels 48 are marked as 1 (black).

CIELAB color space is defined by the following equations:

$$L=116\cdot[(Y/Y0)^{1/3}-16/166]$$

$$a=500\cdot[(X/X0)^{1/3}-(Y/Y0)^{1/3}]$$

$$b=500\cdot[(Y/Y0)^{1/3}-(Z/Z0)^{1/3}]$$

where X, Y, Z is obtained from RGB values using the following equations:

$$X=0.490R+0.310G+0.200B$$

$$Y=0.177R+0.812G+0.011B$$

$$Z=0.000R+0.010G+0.990B$$

and (X0, Y0, Z0) are reference white points (R=255, G=255, B=255).

The method of the Bayesian Weighted K-Means Algorithm is discussed below. Given K feature space classes, a set of K initial n-dimensional cluster centers, $\mu_k$, a set of n-dimensional feature vectors, $x_j$, j=1 . . . N, and a K-dimensional weighting vector $w=[1/K \ldots 1/K]^T$, and assuming spherical Gaussian clusters, each feature vector, $x_j$, is first assigned to a cluster i such that the equation $$\min_k(e_k(x_j)=\|x_j-\mu_k\|/w_k) \qquad (1)$$

is satisfied. New cluster centers, $\mu_k$, and covariance matrices, $\Sigma_k$, are then calculated based on these feature assignments. Note that as the weight assigned to a cluster grows, the likelihood of individual features being assigned to that cluster increases, and the computational complexity is still of the order, O(N·K·n).

A novel aspect of the algorithm involves the process of updating the cluster weight vector using Bayes decision theory. The computationally expensive section of the Bayesian learning method involves the calculation of the n-dimensional Gaussian decision function, $d_k(x_j)$, over each cluster, k, k=1 . . . K, and each feature vector, $x_j$, j=1 . . . N. Thus, the time complexity is O(N·K·n²). However, instead of calculating the decision function for each feature vector and each cluster, the decision surface $D_{r,s}(x)$ between adjacent clusters r and s is calculated in the Bayesian Weighted K-Means algorithm. The time complexity for this additional step is O(K²·n²), which is significantly smaller than O(N·K·n²) for the typical image processing task where N is large. The weight $w_r$ of cluster r and $w_s$ of cluster s are calculated based on the distance f(r,s) between cluster center $\mu_r$ and decision surface $D_{r,s}(x)$ and f(s,r) between cluster center $\mu_s$ and decision surface $D_{r,s}(x)$ using $$f(r,s)/w_r=f(s,r)/w_s, \text{ where } r=1 \ldots K \text{ and } r \neq s \qquad (2)$$

where, $$f(r,s)=\|\mu_r-D_{r,s}(x)\| \qquad (3)$$

$$f(s,r)=\|\mu_s-D_{r,s}(x)\|. \qquad (4)$$

The decision surface $D_{r,s}(x)$ for n-dimensional Gaussian distribution has the form $$\ln p_r - \frac{1}{2}\ln|\sum_r| - \frac{1}{2}\left[(x-\mu_r)^T \sum_r^{-1}(x-\mu_r)\right] - \left(\ln p_s - \frac{1}{2}\ln|\sum_s| - \frac{1}{2}\left[(x-\mu_s)^T \sum_s^{-1}(x-\mu_s)\right]\right) = 0 \qquad (5)$$

which can be written in general quadratic form as $$x^T \cdot A \cdot x + b^T \cdot x + c = 0 \qquad (6)$$

where A is n x n matrix, b is n-dimensional vector and c is a scalar. The distance f(r,s) from each cluster center to the proper decision boundary can be calculated as below.

Let l(x) be the line that passes through $\mu_r$ and $\mu_s$.

Compute intersection z of l(x) and decision surface $D_{r,sj}(x)$.

Let P(x) be the tangential hyper-plane of decision surface $D_{r,sj}(x)$ at point z.

Compute the distance, f(r,s), from $\mu_r$ to P(x).

Because the weighting vector w has K unknowns, K constraints are needed for a solution. From Equation (2), for all the possible combinations of r and s, K−1 of them are independent. Let r=1 . . . K−1 and s=r+1, equation (2) can be written as $$G \cdot w = 0 \tag{7}$$

where $$G = \begin{bmatrix} f(2,1) & -f(1,2) & 0 & 0 & 0 \\ 0 & f(3,2) & -f(2,3) & 0 & 0 \\ 0 & 0 & \ldots & \ldots & 0 \\ 0 & 0 & 0 & f(K,K-1) & -f(K-1,K) \end{bmatrix}_{(K-1) \times K} \tag{8}$$

Equation (7) is a homogeneous system with $K-1$ equations, $K$ unknowns and $\text{rank}(G) = K-1$. A solution for the weighting vector up to a scale, $w'$, can be found from equation (7) using SVD (Singular Value Decomposition). The solution $w'$ is the eigenvector corresponding to the smallest eigenvalue of $G^T G$. In addition, $$\Sigma w = 1 \tag{9}$$

Thus, the actual weighting vector is determined by $$w = w'/\Sigma(w') \tag{10}$$

Once the weighting vector has been updated, the entire assign-update procedure is repeated until the cluster centers and weights converge to a stable value.

Note that calculating the intersection of a line with a general quadratic can be computationally burdensome for high dimensional feature spaces. Because the decision surfaces are used for updating of the weighting vector instead of dividing the patterns into classes, dominant modes can be used to approximate a lower order, $p<n$, decision surface. Thus, in the current implementations of the algorithm, lower dimensional features, $x'$, are used in Equations (3) to (6) to solve for the weighting vector. The one-dimensional and two-dimensional cases are discussed below.

In the case with one dominant discriminatory mode, the lower dimensional feature vector $x'$ becomes a scalar $x$, $\mu_r$ becomes a scalar $u_r$, $\mu_s$ becomes a scalar $u_s$, and the decision surface $D_{r,s}(x)$ is given by the parabola $$a \cdot x^2 + b \cdot x + c = 0 \tag{11}$$

Thus, the quadratic formula can be used to solve for the decision point between two adjacent clusters, $$x_{1,2} = \frac{-b \pm \sqrt{b^2 - 4ac}}{2a} \tag{12}$$

Letting $T = x_{1,2}$ where $T$ is chosen such that, $\mu_r < T < \mu_s$, the distance from each cluster center can be computed using $$f(r,s) = \|\mu_r - D_{r,s}(x)\| = |\mu_r - T| \tag{14}$$

and $$f(s,r) = \|\mu_s - D_{r,s}(x)\| = |\mu_s - T| \tag{15}$$

In the case of two discriminatory modes, the feature vector $x'$ reduces to a point $(x, y)$, $\mu_r$ becomes a point $(u_r, v_r)$; $\mu_s$ becomes a point $(u_s, v_s)$ and the decision surface $D_{r,s}(x)$ is given by the ellipsoid:

$$A \cdot x^2 + B \cdot x \cdot y + C \cdot y^2 + D \cdot x + E \cdot y + F = 0 \tag{16}$$

Figure 10:
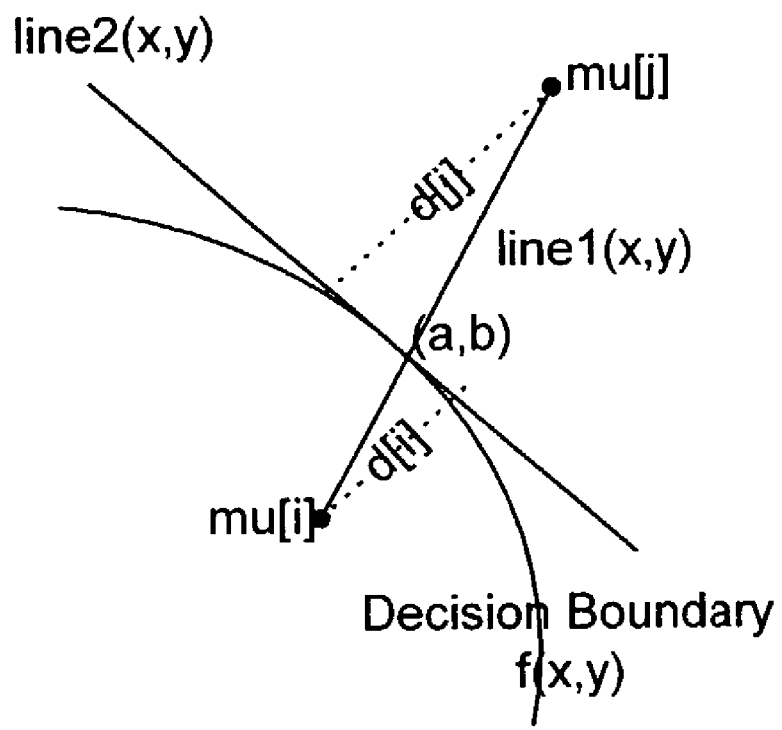
FIG. 10 is an illustration depicting how to compute the distance between cluster center and decision boundary employing the present invention.

The distance $f(r,s) = \|\mu_r - D_{r,s}(x)\|$ can be calculated as below (see FIG. 10):

Let $l_1(x,y)$ be the line that passes through $\mu_r$ and $\mu_s$ $$y - v_r = (v_s - v_r)/(u_s - u_r) \cdot (x - u_r) \tag{17}$$

Compute the intersection $(a,b)$ of $l_1(x,y)$ and curve $D_{r,s}(x,y)$.

Compute $$\frac{\partial y}{\partial x} = -\frac{2 \cdot A \cdot x + B \cdot y + D}{B \cdot x + 2 \cdot C \cdot y + E} = -\frac{2A \cdot a + B \cdot b + D}{B \cdot a + 2 \cdot C \cdot b + e} \tag{18}$$

Let $l_2(x,y)$ be the line that passes through $(a,b)$ and has the slope, $\partial y/\partial x$ such that $$y - b = \partial y/\partial x \cdot (x - a). \tag{19}$$

Figure 11:
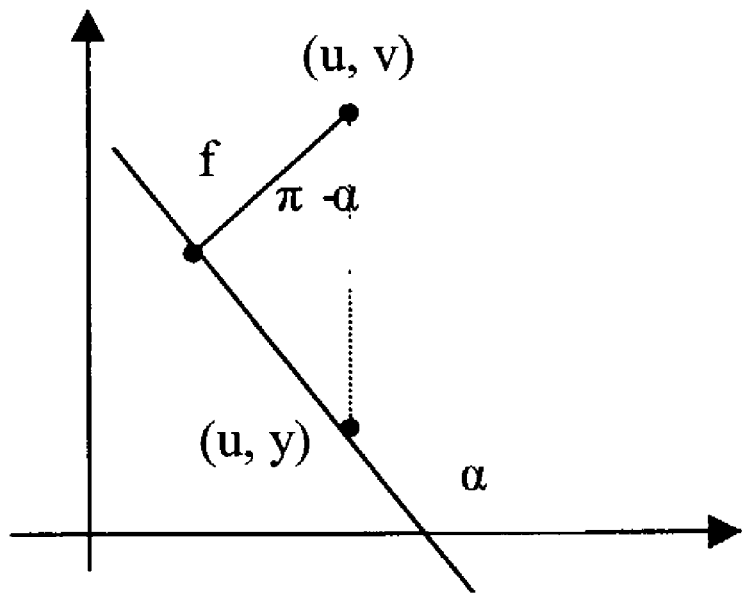
FIG. 11 is an illustration depicting how to compute the distance between cluster center and the tangent of decision boundary employing the present invention.

Compute the distance from $(u_r, v_r)$ to $l_2(x,y)$ (see FIG. 11) using $$f(r,s) = |v_1 - y| \cdot \cos(\pi - \alpha), \text{ where } \alpha = \tan^{-1}(\partial y/\partial x). \tag{20}$$

A complete listing of the algorithm is provided below.

Assumptions:

Each cluster is modeled by a spherical Gaussian distribution

Input Data:

Pattern Set—$X = \{x \text{ in } R^n | x, j=1 \ldots N\}$

Number of Clusters—$K$

Initial Cluster Centers—$\mu_k$ in $R^n$, $k=1 \ldots K$

Initial $K$-dimensional weighting vector, $w = [1/K \ldots 1/K]^T$

A priori probability of cluster—$p_k$

Steps:

1. For each feature vector $x_j$, compute $e_k(x_j) = \|x_j - \mu_k\|/w_k$ for each cluster center, $\mu_1$. Find the minimal value of $e_k(x_j)$ with respect to $k$ for each feature vector. Assign pattern $x_j$ to cluster $k$.

2. Compute new cluster centers $\mu_k$ and covariance matrices $\Sigma_k$ for each cluster.

3. Update the weighting vector $w$.

a) For cluster $r$ and $s = r+1$ where $r = 1 \ldots K-1$, compute the decision surface $D_{r,s}(x')$ using Bayes decision theory, where $x'$ is a subset of size one or two selected from $x$ to reduce the computational complexity of the decision surface.

b) Compute the distance from each cluster center to the appropriate decision surface $$f(r,s) = \|\mu_r - D_{r,s}(x')\| \tag{21}$$

and $$f(r,s) = \|\mu_s - D_{r,s}(x')\| \tag{22}$$

c) Let $$f(r,s)/w_r = f(s,r)/w_s, \ r = 1 \ldots K-1, \ s = r+1. \tag{23}$$

d) Use the expression $$G \cdot w = 0 \quad (24)$$

where $$G = \begin{bmatrix} f(2,1) & -f(1,2) & 0 & 0 & 0 \\ 0 & f(3,2) & -f(2,3) & 0 & 0 \\ 0 & 0 & \ldots & \ldots & 0 \\ 0 & 0 & 0 & f(K, K-1) & -f(K-1, K) \end{bmatrix}_{(K-1) \times K} \quad (25)$$

and the normalizing constraint $$\Sigma(w) = 1 \quad (26)$$

to solve for a new weighting vector w.

4. If the old model and new model parameters, $\{\mu, w\}$, are sufficiently close to each other, terminate, else return to step 1.

B. Particle Recognition Module

Figure 1:
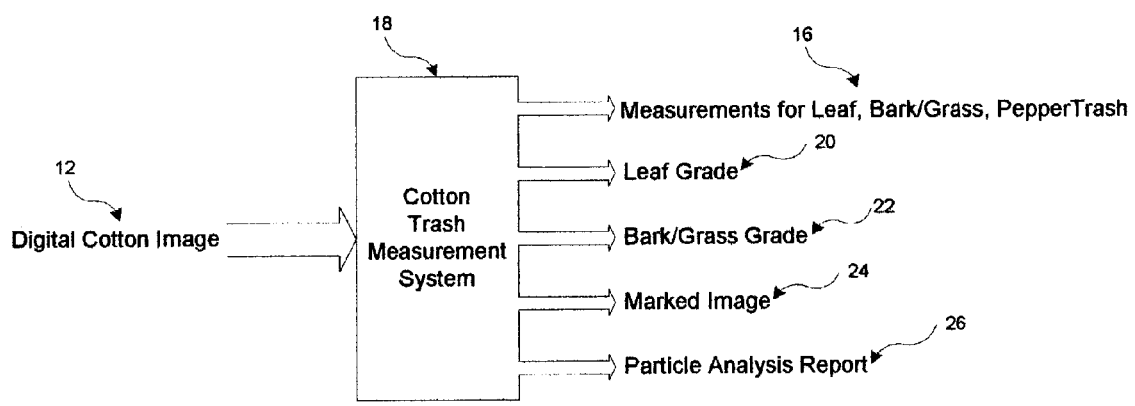
FIG. 1 is a generalized schematic flow diagram of one embodiment of a system of the present invention.
Figure 2:
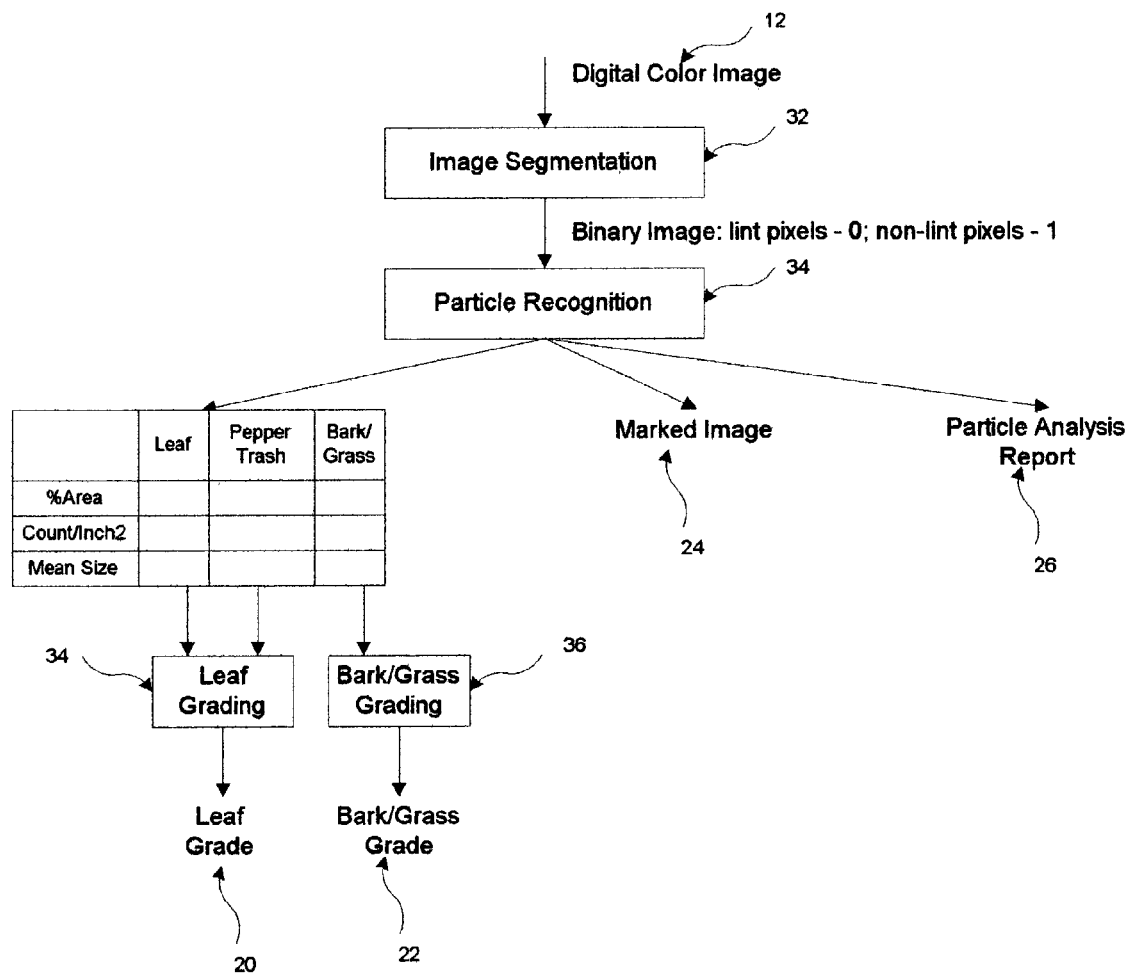
FIG. 2 is a detailed schematic flow diagram of the embodiment of the present system depicted in FIG. 1.
Figure 3:
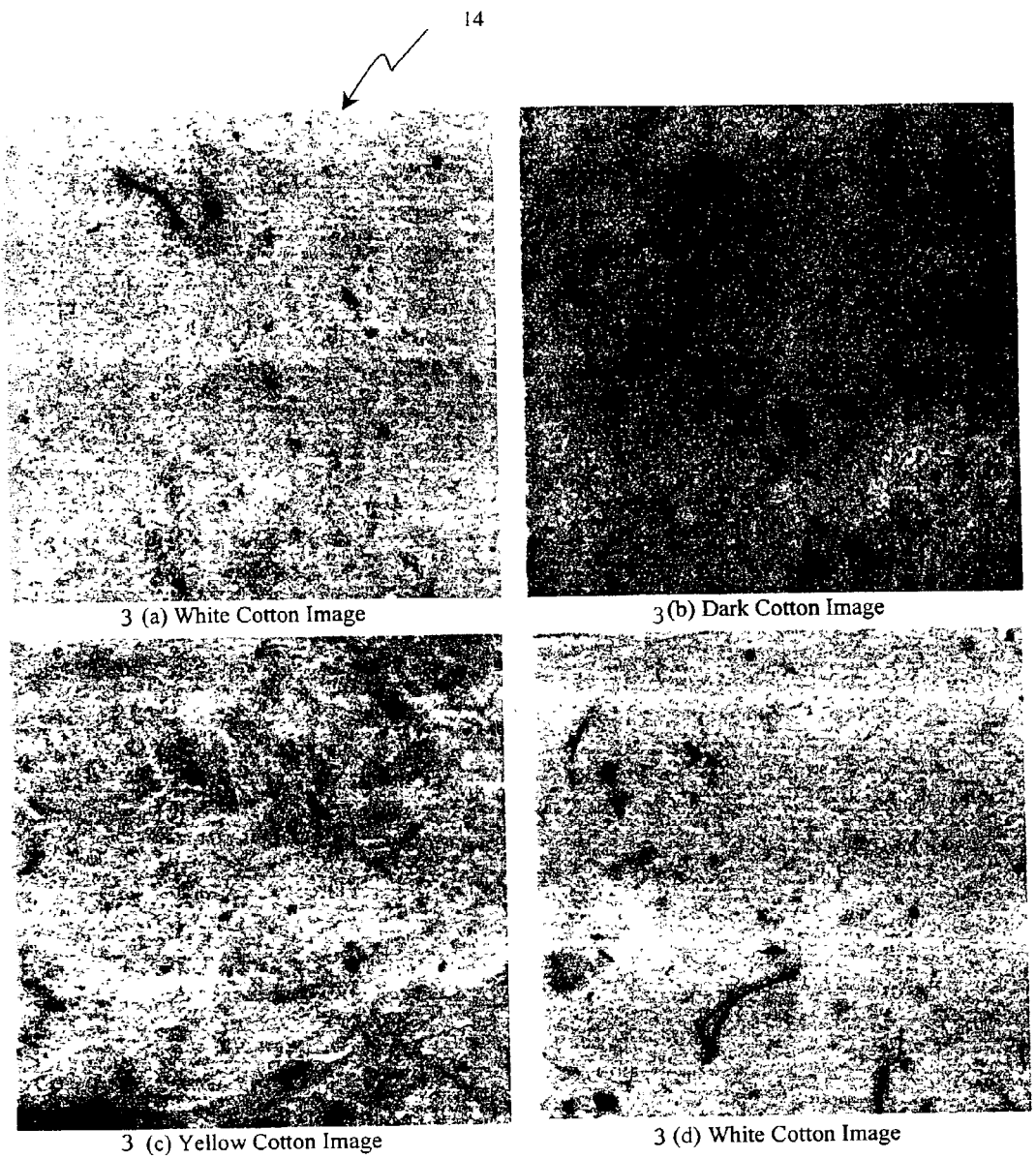
FIGS. 3a, 3b, 3c and 3d depict four examples of input images (in black and white) depicting different colors and particles in the samples of cotton samples and trash.
Figure 12:
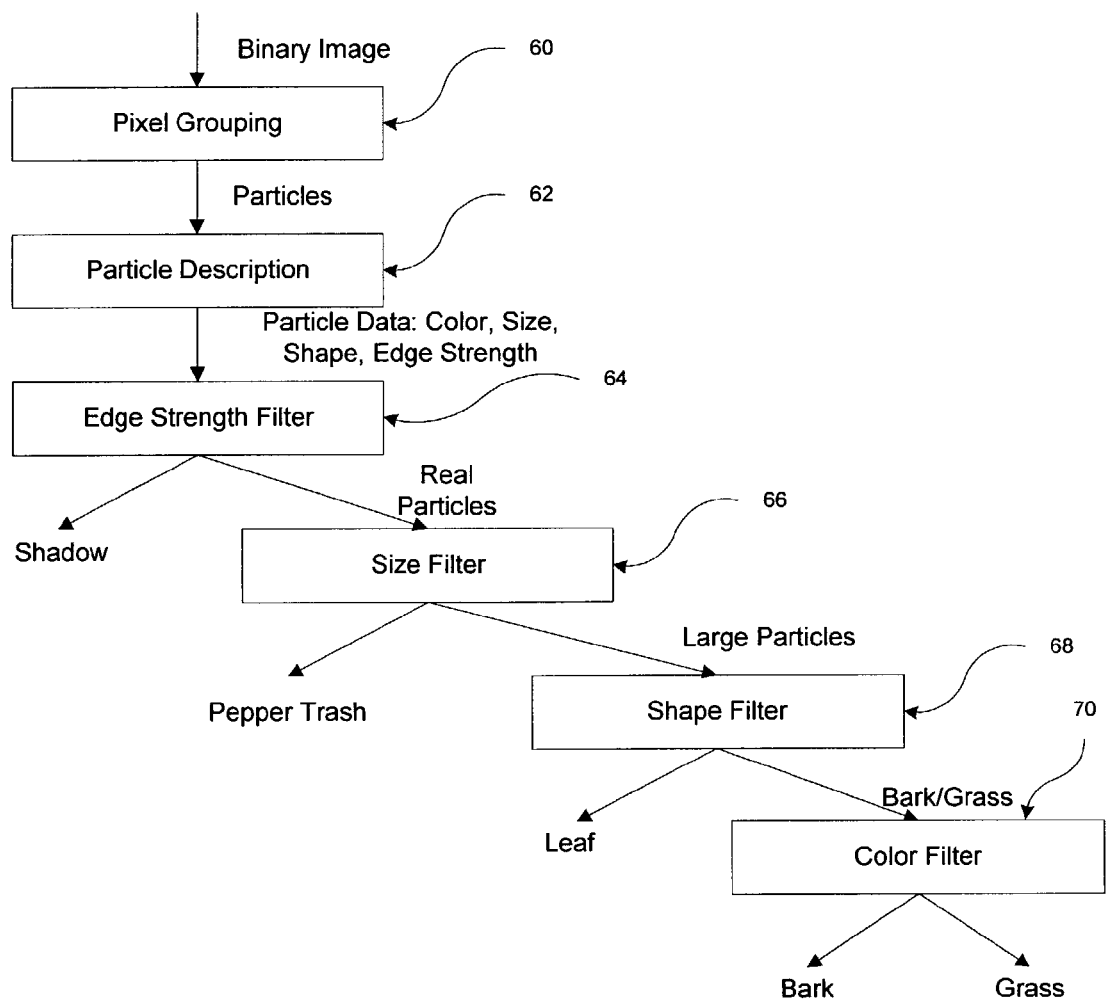
FIG. 12 is a generalized flow diagram of one embodiment of a particle recognition module as employed in the present invention.

FIG. 12 depicts a generalized flow diagram of one embodiment of the process of particle recognition module 34. The objective of this module is to categorize and analyze the non-lint regions 48 identified in the image segmentation module 32. This module 24 outputs measurements 16 for leaf, bark/grass and pepper trash, marked image 24 and the particle analysis report 26 (see FIG. 1).

Figure 13:
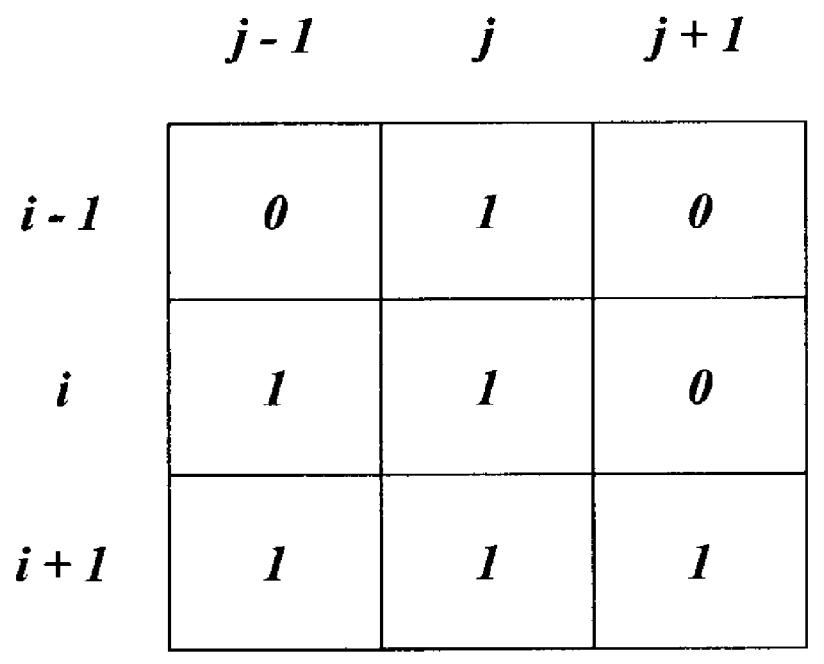

The first step of particle recognition is pixel grouping 60. This step applies connected components labeling algorithm to process input binary image 50. The connected non-lint pixels are grouped as particles based on 8-connectivity (see FIG. 13). In 8-connectivity, the pixel (i, j) is connected with neighbor pixels (i−1, j−1), (i−1, j), (i−1, j+1), (i, j−1), (i, j+1), (i+1, j−1), (i+1, j) and (i+1, j+1) as shown in FIG. 13. Denote i means ith row and j means jth column in the image. Image(i, j) means the value of pixel (i, j). Label(i, j) means the label that is assigned to pixel (i, j). After connected components labeling, every pixel will be assigned a label and the pixels in the sample particle will be assigned the same label.

The connected components labeling operator scans the binary image from left to right and from top to bottom until it comes to a pixel (i, j) for which Image(i, j)=1 (non-lint pixel). The operator checks four of the neighbors of (i, j) which have already been encountered in the scan. They are pixels (i−1, j−1), (i−1, j), (i−1, j+1), and (i, j−1). If all four neighbors have value of 0, assign a new label to (i, j). If only one neighbor has value of 1, assign its label to (i, j). If more than one neighbors have value of 1, assign maximal label to (i, j) and record the equivalence between all other labels and the maximal label. After completing the scan, the equivalent label pairs are sorted into equivalence classes and a unique label is assigned to each class. As a final step, a second scan is made through the image, during which each label is replaced by the label assigned to its equivalence classes.

Figure 14:
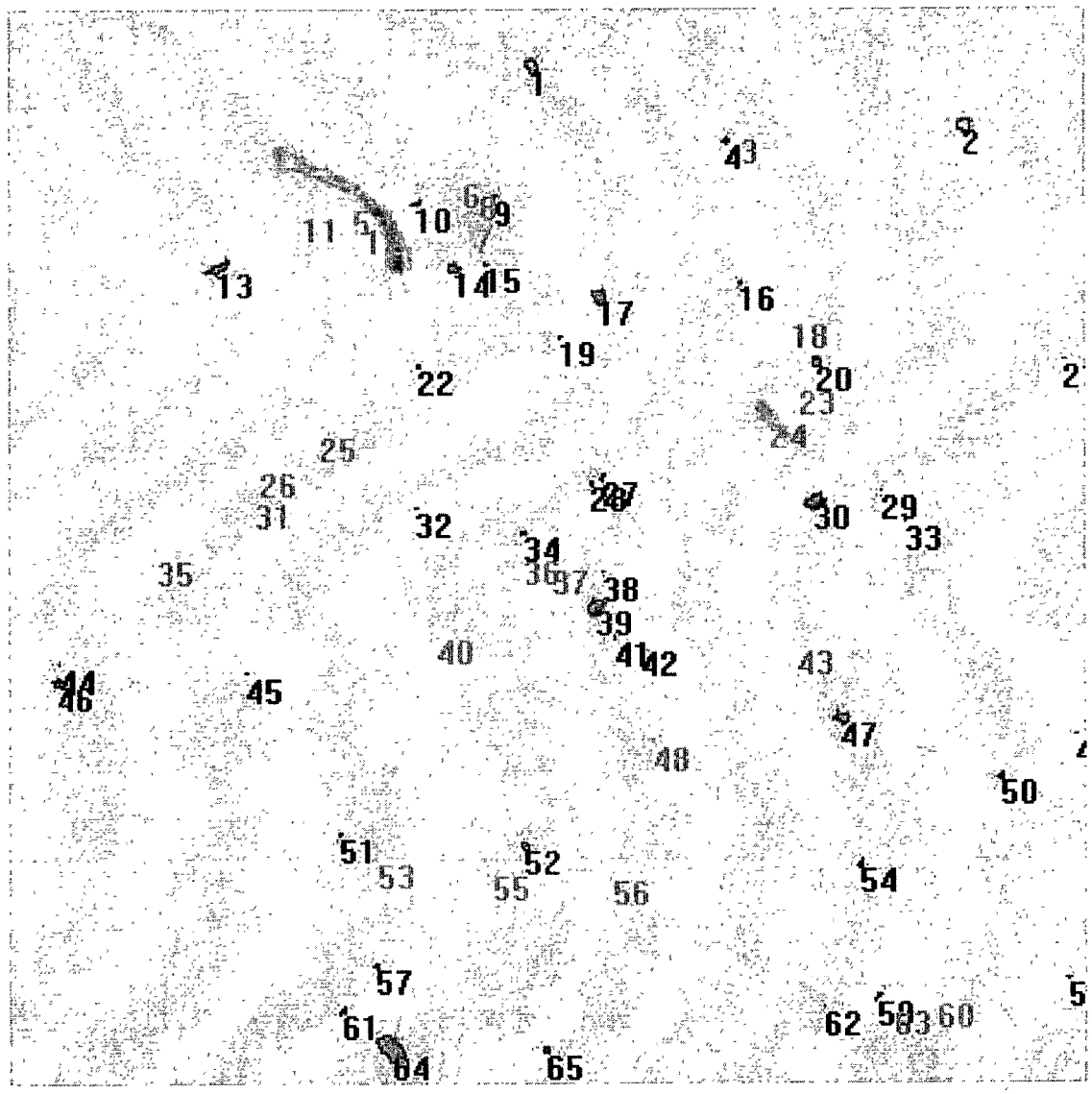
FIG. 14 depicts one example of a labeled image produced by the particle recognition module of the present invention.

As shown in FIG. 14, the labeled image, all the pixels are grouped into particles and each particle is assigned a label as particle id.

The following step describes particle description 62. Color, size, shape and edge strength is computed for each particle. The algorithm is shown below.

Size—the square root of particle area.
PixelCount=0
For each pixel in the particle,
    PixelCount=PixelCount+1,
End For
Size=sqrt(PixelCount)/150 dpi*25400 micron/inch
    Color—the average color of all the pixels in the particle in CIELAB color space.
Particle.Color=0
For each pixel in the particle,
    Particle.Color=Particle.Color+Pixel.Color,
End For
Particle.Color=Particle.Color/PixelCount
    Shape—thinness, the ratio of particle length and width.
Compute the covariance matrix of the distance from pixels to particle center:
Center.x=0
Center.y=0
For each pixel in the particle,
    Center.x=Center.x+Pixel.x,
    Center.y=Center.y+Pixel.y
End For
Center.x=Center.x/PixelCount
Center.y=Center.y/PixelCount
XX=0
XY=0
YY=0
For each pixel in the particle
    Dx=Pixel.x−Center.x
    Dy=Pixel.y−Center.y
    XX=XX+Dx*Dx/PixelCount
    XY=XY+Dx*Dy/PixelCount
    YY=YY+Dy*Dy/PixelCount
End For
ConvarianceMatrix=[XX, XY
    XY, YY]
Compute the eigenvalues of the covariance matrix:
The characteristic polynomial is:
eig^2−(XX+YY)*eig+XX*YY−XY^2=0
eig1=½*[(XX+YY)+sqrt(XX^2−2*XX*YY+YY^2+4*XY^2)]
eig2=½*[(XX+YY)−sqrt(XX^2−2*XX*YY+YY^2+4*XY^2)]
Length=eig1
Width=eig2
Thinness=Length/Width
    Edge Strength—average edge strength of all the pixels in the particle
Apply the Sobel filter:
[−1 −2 −1
  0  0  0
  1  2  1] and
[−1 0 1
 −2 0 2
 −1 0 1] to each pixel in the particle
EdgeStrength=0
For each pixel in the filtered particle,
    EdgeStrength=EdgeStrength+PixelValue,
End For
EdgeStrength=EdgeStrength/PixelCount
    Each particle with the description of color, size, shape and edge strength is then passing through four filters 64, 66, 68 and 70 as shown in FIG. 12. Edge strength filter 64 blocks all the shadows and allows all of the real particles to pass through. Size filter 66 blocks all the pepper trash and allows all of the large particles to pass through. Shape filter 68 blocks all the leaf and allows all of the bark/grass particles to pass through. Finally, the color filter 70 separates the bark and grass. The filtering result is then utilized to mark the image, generate the particle analysis report and compute the measurements of leaf, pepper trash and bark/grass.

C. Leaf Grading Module

Figure 15:
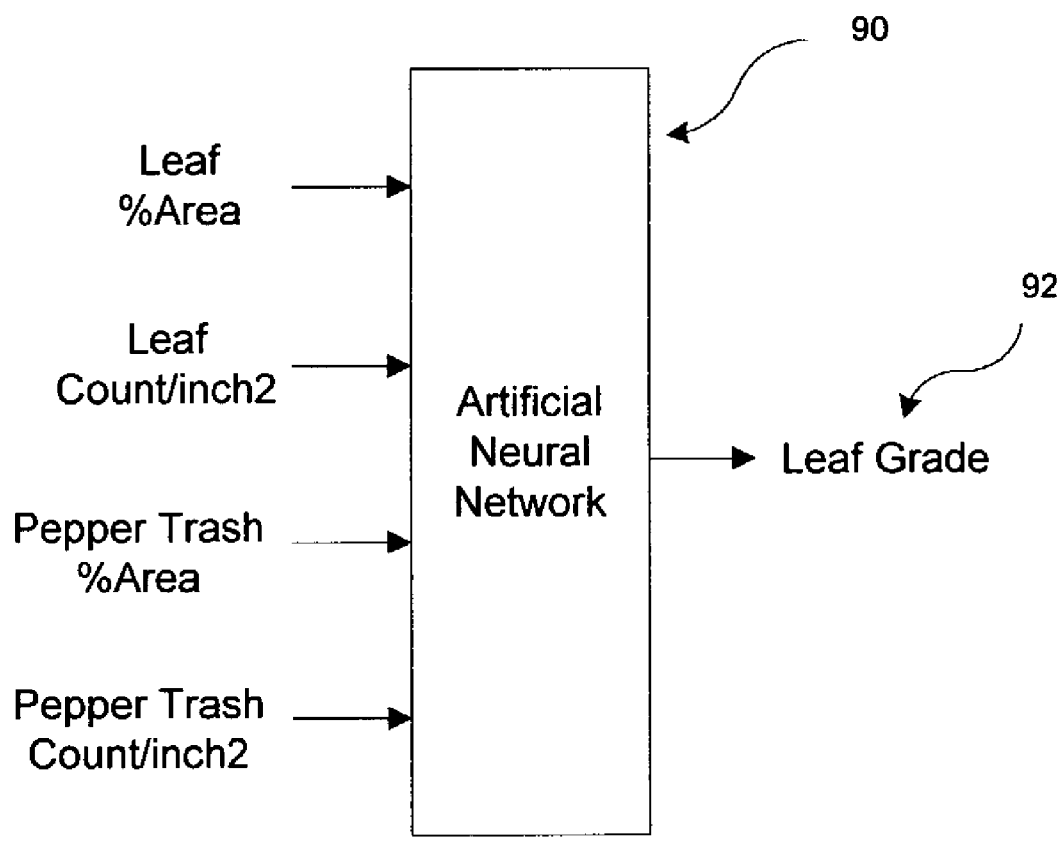
FIG. 15 is a generalized flow diagram of one embodiment leaf grading module as employed in the present invention.

Following the image segmentation and particle recognition modules, all kinds of trash particles are measured and classified. What will finally determine the cotton market value, however, is the Leaf Grade and Bark/Grass Grade. A generalized flow diagram of one embodiment of a Leaf Grading module 90 is depicted in FIG. 15. This module is designed to develop the Leaf Grade 9 based on the measurements and classifications of all the trash particles. In the industry, there are seven leaf grades, designated as leaf grade "1" through "7". Leaf grade 1 represents lowest leaf content or highest quality of cotton. In the present invention, Artificial Neural Network is employed in this module to estimate the Leaf Grade based on the percentage surface area occupied by leaf particles, leaf particles count per inch squared, percentage surface area occupied by pepper trash, and pepper trash particles count per inch squared as shown in FIG. 15.

Figure 16:
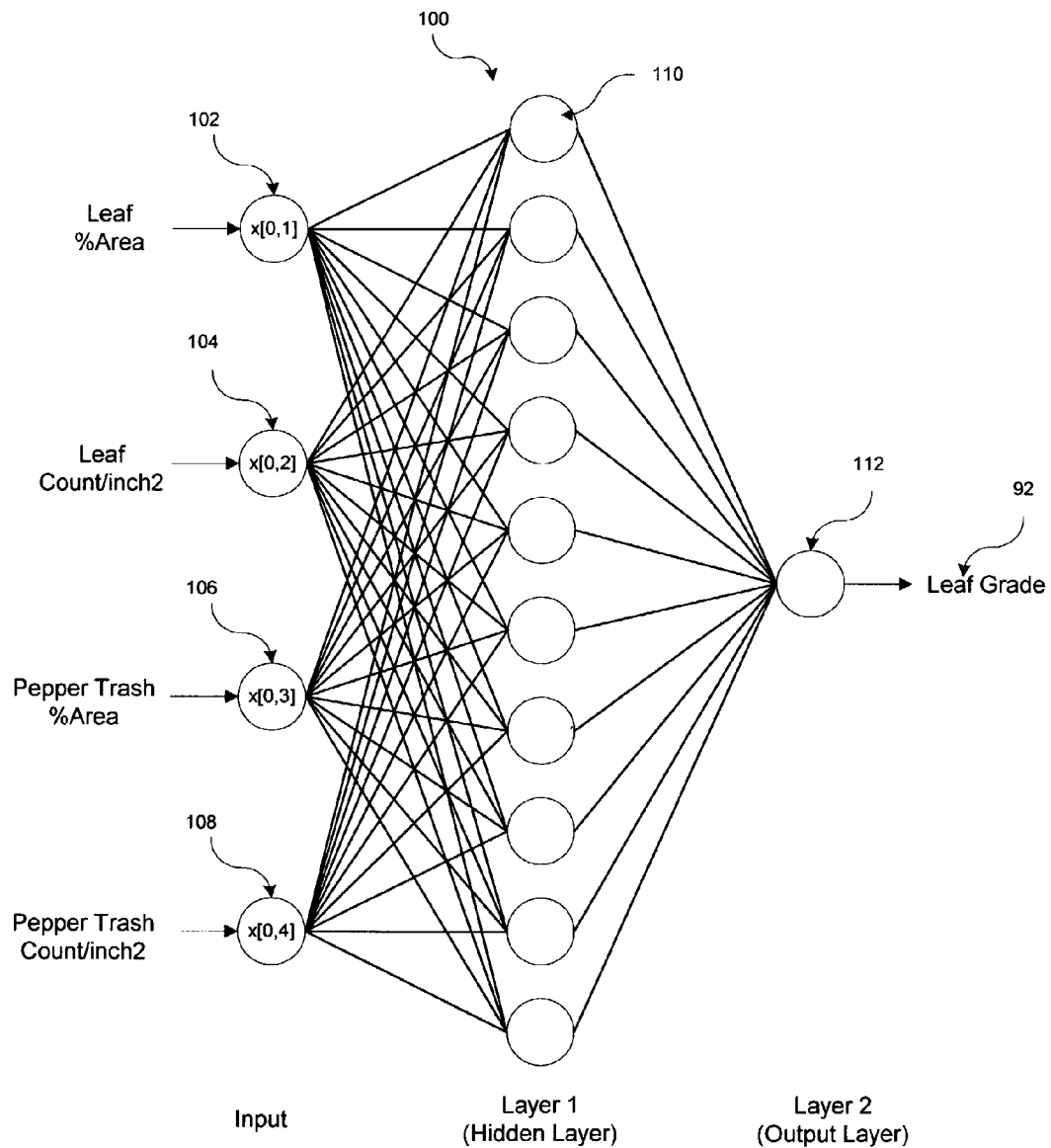
FIG. 16 is a diagrammatic representation of an artificial neural network architecture as employed in a leaf grading module of the present invention.
Figure 17:
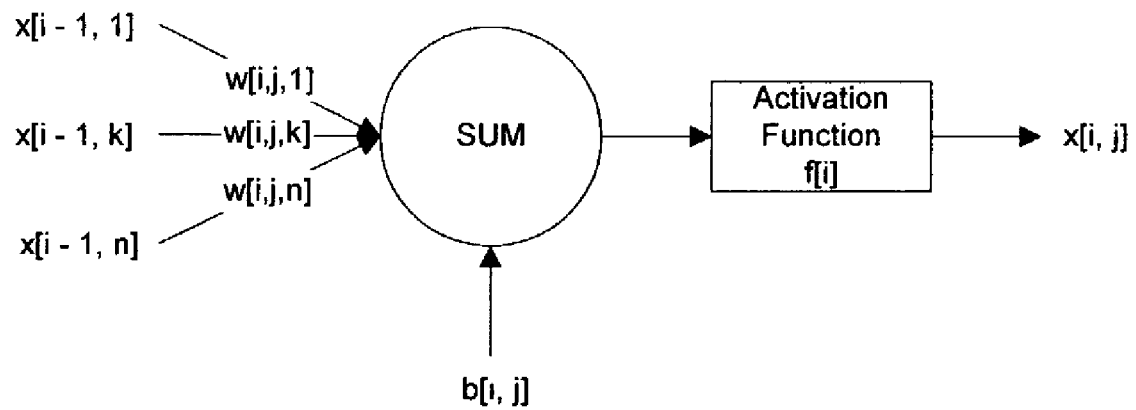
FIG. 17 is a diagrammatic representation of one embodiment of a single neuron structure as employed in the present invention.

As shown in FIG. 16, a two-layer feed forward neural network 100 with four inputs 102, 104, 106 and 108, ten hidden neurons 110 (typical) and one output 112 is constructed. Each neuron in layer 1 and layer 2 has the structure as show in FIG. 17. The mathematical model of neuron [i, j] is $$x_{i,j} = f_i(x_{i-1,1}*w_{i,j,1} + \ldots + x_{i-1,k}*w_{i,j,k} + \ldots + x_{i-1,n}*w_{i,j,n} + b_{i,j}) \quad (27)$$

where i stands for i th layer, j stands for j th neuron in a layer, $x_{i,j}$ is the output of neuron [i, j], $X_{i-1,k}$ is the output of neuron [i-1, k], $w_{i,j,k}$ is the weight of connection between neuron [i, j] and neuron [i-1, k], $b_{i,j}$ is the bias of neuron [i, j] and $f_i(\ )$ is the activation function of i th layer. In Leaf Grading module, the activation function for layer 1 is hyperbolic tangent function:

$$f_1(x) = 2/(1+\exp(-2*x)) - 1 \quad (28)$$

The activation function for layer 2 is pure linear function:

$$f_2(x) = x \quad (29)$$

Let m be the number of neurons in layer i and n be the number of neurons in layer i−1. The m outputs for i th layer will be:

$$x_{i,1} = f_i(x_{i-1,1}*w_{i,1,1} + \ldots + x_{i-1,k}*w_{i,1,k} + \ldots + x_{i-1,n}*w_{i,1,n} + b_{i,1})$$

$$x_{i,j} = f_i(x_{i-1,1}*w_{i,j,1} + \ldots + x_{i-1,k}*w_{i,j,k} + \ldots + x_{i-1,n}*w_{i,j,n} + b_{i,j}) \quad (30)$$

$$x_{i,m} = f_i(x_{i-1,1}*w_{i,m,1} + \ldots + x_{i-1,k}*w_{i,m,k} + \ldots + x_{i-1,n}*w_{i,m,n} + b_{i,m})$$

The matrix format of Equation (30) is $$x_i = f_i(W_i \cdot x_{i-1} + b_i) \quad (31)$$

where $x_i$ is m-dimensional output vector of i th layer, $W_i$ is m x n weight matrix of i th layer, and $b_i$ is m-dimensional bias vector of i the layer.

For Leaf Grading module, the mathematical model is $$x_1 = f_1(W_1 \cdot x_0 + b_1) \quad (32)$$

$$x_2 = f_2(W_2 \cdot x_1 + b_2)$$

where $W_1$ is the 10×4 weight matrix of layer 1, $b_1$ is the 10-dimensional bias vector for layer 1, $W_2$ is the 1×10 weight matrix of layer 2, $b_2$ is the bias for layer 2. $x_0$ is the 4-dimensional input vector (Leaf % Area, Leaf Count/inch$^2$, Pepper Trash % Area, Pepper Trash Count/inch$^2$), $x_1$ is 10-dimentional vector and x2 is the Leaf Grade.

The Artificial Neural Network must be trained using leaf standard and hundreds of cotton samples with known leaf grade. The weight matrix $W_1$ and $W_2$ and bias vector $b_1$ and b2 will be determined in the training process. The training algorithm used here is Levenberg-Marquardt algorithm. The algorithm is performed in off-line, or batch, mode, where the weight matrixes and bias vectors are only updated after a complete scan through the whole training set. The Levenberg-Marquardt algorithm is a non-linear least squares algorithm. It is an approximation to Gauss-Newton method. The algorithm is described below.

The performance index for the network is $$V = \frac{1}{2} \sum_{q=1}^{Q} (t^q - x_M^q)^T (t^q - x_M^q) = \frac{1}{2} \sum_{q=1}^{Q} (e^q)^T e^q \quad (33)$$

where Q is the number of input vectors in data set, $x_M^q$ is the output of the network when the q th input vector, $x_0^q$, is presented, $t^q$ is the target of the q th input, and $e^q = t^q - x_M^q$ is the error for q th input. In Leaf Grading module, M=2 and the target $t^q$ and output $x_2^q$ are scalars. Thus, $$V = \sum_{q=1}^{Q} (t^q - x_M^q)^2 = \sum_{q=1}^{Q} (e^q)^2 \quad (34)$$

Since $x_2^q$ is a function of $W_1$, $b_1$, $W_2$ and b2, let $$y = [w_{1,1,1}, \ldots w_{1,10,4}, b_{1,1}, \ldots w_{2,1,1}, \ldots w_{2,1,10}, b_{2,1}]^T \quad (35)$$

Thus, $$V(y) = \sum_{q=1}^{Q} [t^q - x_M^q(y)]^2 = \sum_{q=1}^{Q} [e^q(y)]^2 \quad (36)$$

We want to minimize V(y) with respect to the parameter vector y, the Levenberg-Marquardt method would be $$\Delta y = [J^T(y)J(y) + \mu I]^{-1} J^T(y) e(y) \quad (37)$$

where Where J(y) is the Jacobian matrix.

$$J(y) = \begin{bmatrix} \frac{\partial e^1(y)}{\partial y_1} & \frac{\partial e^1(y)}{\partial y_2} & \cdots & \frac{\partial e^1(y)}{\partial y_{61}} \\ \frac{\partial e^2(y)}{\partial y_1} & \frac{\partial e^2(y)}{\partial y_2} & \cdots & \frac{\partial e^2(y)}{\partial y_{61}} \\ \vdots & \vdots & \ddots & \vdots \\ \frac{\partial e^Q(y)}{\partial y_1} & \frac{\partial e^Q(y)}{\partial y_2} & \cdots & \frac{\partial e^Q(y)}{\partial y_{61}} \end{bmatrix} \quad (38)$$

The parameter μ is multiplied by some factor (β) whenever a step would result in an increased V(y). The algorithm adjusts μ, and then computes $y_{new}=y+\Delta y$ until $V(y_{new})$ is decreased. When a $\Delta y$ that decreases $V(y)$ is found, y is updated using $y=y+\Delta y$. The algorithm iteratively update y until the objective of the performance index $V(y)$ is achieved.

After training, the Artificial Neural Network is ready to accept the measurements and produce leaf grade. The output of the network is presented in one decimal leaf grade (e.g., 2.4) to provide more accurate representation of leaf content than traditional 7-level leaf grade. It is easy to convert the decimal leaf grade to traditional 7-level leaf applying round-to-nearest-integer method. For example, decimal leaf grade 3.3 will be converted to traditional leaf grade 3 and leaf grade 3.7 will be converted to traditional leaf grade 4.

D. Bark/Grass Grading Module

Figure 18:
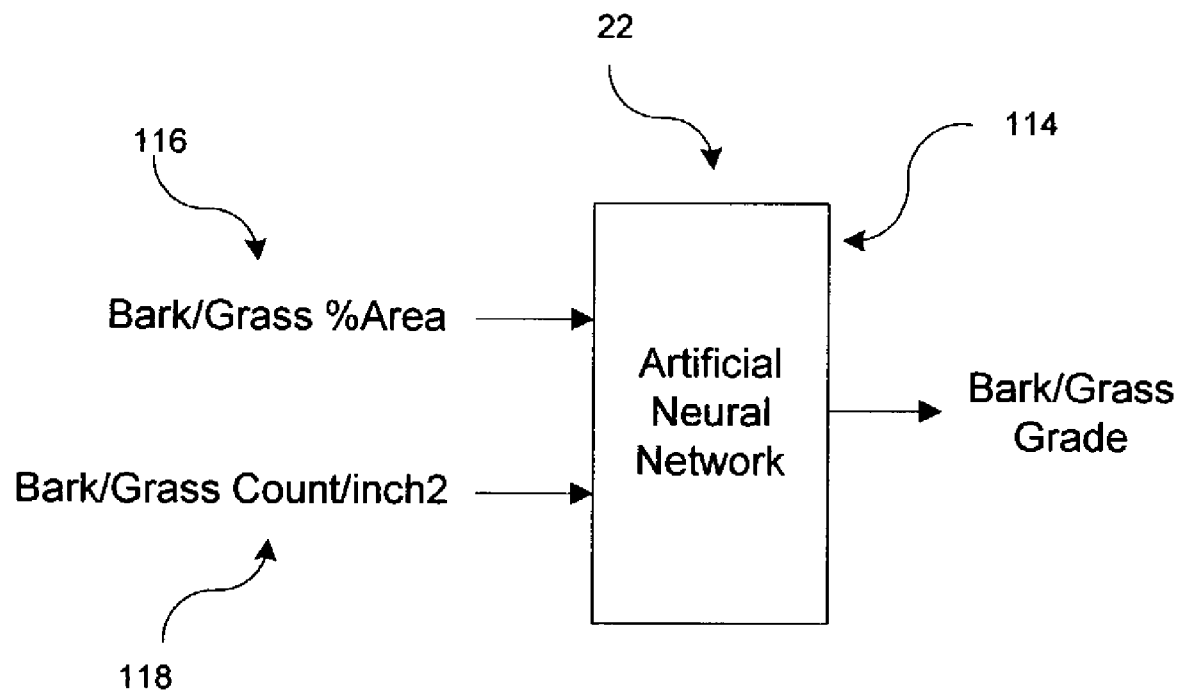
FIG. 18 is a generalized flow diagram of one embodiment of a bark/grass grading module as employed in the present invention.

The objective of Bark/Grass Grading module 22 is to produce Bark/Grass Grade based on the measurement. There are three different Bark/Grass Grading levels designated as "0" through "2". Bark/Grass Grade "0" means there are no Bark/Grass in the cotton, Bark/Grass Grade "1" means bark/grass content in cotton is light and Bark/Grass Grade "2" means bark/grass content is heavy. A generalized flow diagram of one embodiment of a Bark/Grass Grading module employs the same Artificial Neural Network 100 technique with the different inputs as shown in FIG. 18. The inputs are percentage surface area 116 occupied by bark/grass particles and the bark/grass particles count per inch squared 118.

Figure 19:
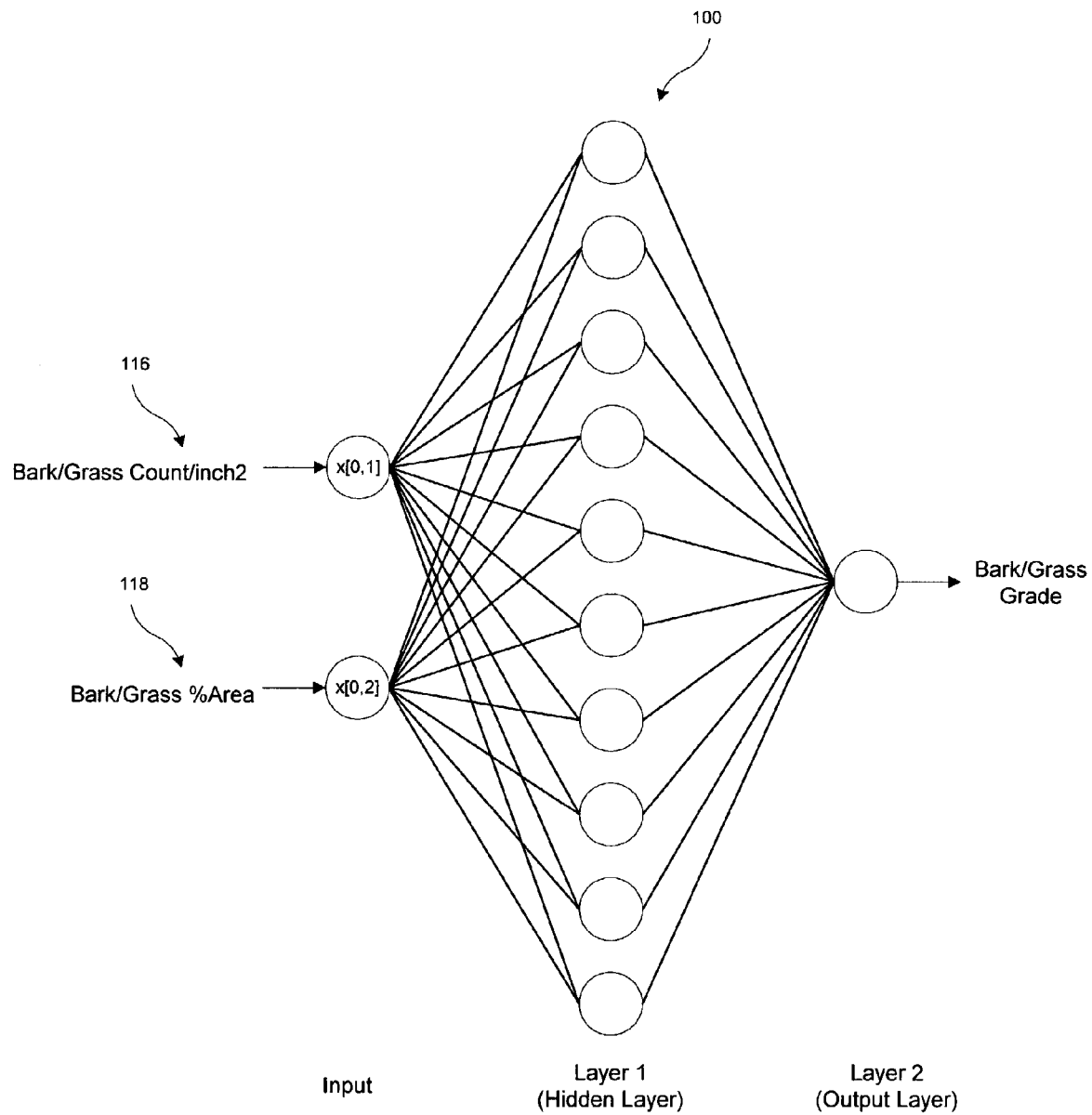
FIG. 19 is a diagrammatic representation of one embodiment of an artificial neural network architecture as employed in a bark/grass grading module of the present invention.

As shown in FIG. 19, a two-layer feed forward neural network with two inputs, ten hidden neurons and one output is constructed. The Artificial Neural Network is also trained by the Levenberg-Marquardt algorithm.

The output of the network is in decimal value between 0 to 2.5. The decimal value will be rounded to an integer based on round-to-nearest-integer method. The rounded value is then reported as Bark/Grass grade.

What is claimed:

1. A method of analysis of a sample of cotton which includes diverse elements comprising the steps of
   a. electro-optically capturing and electronically processing a digital image of said sample, said digital image including representations of each of a plurality of the diverse elements of this sample,
      i. scanning the sample of cotton to develop a digital image of said sample, said digital image including representations of each of a plurality of the diverse elements of the sample,
      ii. identifying substantially each pixel of said digital image as lint pixel or non-lint pixel,
      iii. grouping adjacent non-lint pixels into individual ones of said diverse elements,
      iv. calculating at least one or more of the color, shape, texture, length/width ratio, and edge strength feature of each of said identified diverse elements,
      v. classifying each of said diverse elements as one of leaf, pepper trash, bark, grass or shadow based on the calculated features of each of said diverse elements,
      vi. calculating percent area and count per inch$^2$ for each class of diverse elements,
   b. providing a computer equipped with an artificial neural network,
   c. training said artificial neural network employing multiple samples of cotton which have been visually examined and assigned a grade by a human, said training including storing within said computer equipped with said artificial neural network, a digital image of each of said multiple samples and their respective grades which have been assigned thereto by the human,
   d. employing said computer and said trained artificial neural network, comparing said existence of, and one or more properties of the sample of cotton to the existence of, and one or more properties of, each of said multiple samples which have been visually examined and assigned a grade by a human and stored in said computer,
   e. outputting from said computer a numerical grade for said sample of cotton which is a function of the degree of similarity of said sample of cotton to a human graded one of said multiple samples stored in said computer.

2. The method of claim 1 wherein the sample comprises cotton fibers and said diverse elements comprise trash disposed within the sample.

3. The method of claim 1 wherein said diverse elements include at least one of leaf, bark, grass, and/or pepper trash.

4. The method of claim 3 wherein one of said diverse elements includes shadows.

5. The method of claim 1 wherein said steps of identifying substantially each pixel of said digital image as lint pixel or non-lint pixel and grouping adjacent non-lint pixels into individual particles, includes evaluation of said pixels employing a Bayesian Weighted K-Means Clustering algorithm.

6. A method of analysis of a sample of raw cotton which includes diverse elements comprising the steps of
   capturing a two-dimensional color digital image of the sample,
   converting said digital image to a binary image wherein each of the pixels of said digital image is assigned a value which identifies the pixel as lint or non-lint,
   grouping at least said non-lint pixels into individual classes of trash having like properties comprising,
      a. calculating at least one or more of the color, shape, texture, length/width ratio, and edge strength feature of each of said diverse elements,
      b. classifying each of said diverse elements as one of leaf, pepper trash, bark, grass or shadow based on the calculated features of each of said diverse elements,
      c. calculating percent area and count per inch$^2$ for each class of diverse elements.
   providing a computer equipped with an artificial neural network,
   training said artificial neural network employing multiple samples of cotton which have been visually examined and assigned a grade by a human, said training including storing within said computer equipped with said artificial neural network, a digital image of each of said multiple samples and their respective grades which have been assigned thereto by the human,
   employing said computer and said trained artificial neural network, comparing said existence of, and one or more properties of the sample of cotton to the existence of, and one or more properties of, each of said multiple samples which have been visually examined and assigned a grade by a human and stored in said computer,
   outputting from said computer a numerical grade for said sample of cotton which is a function of the degree of similarity of said sample of cotton to a human graded one of said multiple samples stored in said computer.

7. The method of claim 6 wherein said samples and associated grades stored in said artificial neural network includes one or more computer-graded samples of cotton and their associated grades.

8. The method of claim 6 wherein said steps of converting said digital image to a binary image wherein each of the pixels of said digital image is assigned a value which identifies the pixel as lint or non-lint, grouping at least said non-lint pixels into individual classes of trash having like properties includes evaluation of said pixels employing a Bayesian Weighted K-Means Clustering algorithm.

9. A method for the grading of a cotton sample which includes diverse trash elements comprising the steps of
  a. developing a two-dimensional color digital image of the sample,
  b. creating a CIELAB color space,
  c. employing a Bayesian Weighted K-Means Clustering Algorithm, classifying the data points in the CIELAB color space to convert said digital image to a binary image,
  d. assigning values to each of the pixels of said binary image,
  e. grouping like ones of said sets into two or more groups,
  f. categorizing and analyzing at least one selected group of said groups employing a connected components labeling algorithm to divide said binary image into sets of coherent regions or objects,
  g. creating a RGB color space employing said two or more groups of values,
  h. analyzing at least one of the color size, shape and edge strength of each categorized selected group,
  i. marking each categorized group as a function of its detected characteristics,
  j. providing a computer equipped with an artificial neural network,
  k. training said artificial neural network employing multiple samples of cotton which have been visually examined and assigned a grade by a human, said training including storing within said computer equipped with said artificial neural network, a digital image of each of said multiple samples and their respective grades which have been assigned thereto by the human,
  l. employing said computer and said trained artificial neural network, comparing said existence of, and one or more properties of the sample of cotton to the existence of, and one or more properties of, each of said multiple samples which have been visually examined and assigned a grade by a human and stored in said computer,
  m. outputting from said computer a numerical grade for said sample of cotton which is a function of the degree of similarity of said sample of cotton to a human graded one of said multiple samples stored in said computer.

10. An image-based method of grading cotton samples, which samples include cotton lint and diverse, non-lint elements, said diverse non-lint elements having localized, differently-responding image features from cotton lint, and comprising the steps of
  a. capturing a digital image of the cotton sample, said digital image including a multiplicity of pixels, each of said pixels having unique and localized spatial position and an amplitude response in proportion to light intensity received thereupon, said multiplicity of pixels comprising an original image file stored in and processed by a digital computer,
  b. employing said digital computer, determining, from the amplitude response for each of said pixels in said digital image of the cotton sample, whether each pixel represents cotton lint or a non-lint element, and assigning binary values of "0" to lint and "1" to non-lint elements disposed within the cotton sample,
  c. grouping one or more adjacent ones of said non-lint pixels into a binary image of said non-lint elements, and storing said binary image within said computer,
  d. employing said binary image and said original image file in said computer, determining one or more image features for each of said non-lint elements,
  e. employing said one or more determined image features, grouping said non-lint elements into one or more classes of cotton trash,
  f. employing said stored original binary image and said determined image files, calculating count per inch$^2$ and percentage area for said one or more determined image features for each of said non-lint elements,
  g. providing a computer having an artificial neural network associated therewith,
  h. introducing to said computer a multiplicity of cotton samples having respective ones of a wide range of human-assigned grades for each class of said non-lint elements, executing steps a-f hereinabove, to thereby train said artificial neural network by measurement of image feature data for each such non-lint classification and associating said measured image feature data with said human-assigned grades, and
  i. thereafter, for an unknown cotton sample, using said measurement data of image features and said trained artificial neural network, outputting instrumental estimates of the grade of said unknown cotton sample corresponding to said diverse, non-lint elements in said unknown sample.

11. The method of claim 10 wherein said steps a-e include analysis of data accumulated in said computer employing a Bayesian K-Means Clustering Algorithm.

12. The method of claim 10 wherein said diverse non-lint elements comprise leaf, pepper trash, bark, grass and shadows.

13. A method of analysis and outputting of a grade for a sample of cotton which includes diverse elements comprising the steps of
  a. providing a computer equipped with an artificial neural network,
  b. training said artificial neural network employing multiple samples of cotton, each of which has been visually examined and assigned at least one grade by at least one human, said training comprising the steps of:
    i. electro-optically capturing and electronically processing a digital image of each of said multiple samples, each of said digital images including representations of each of a plurality of the respective diverse elements of said multiple samples,
    ii for each of said multiple samples, identifying substantially each pixel of each of said digital images as a lint pixel or a non-lint pixel,
    iii. grouping adjacent non-lint pixels of respective ones of said multiple samples into individual ones of said diverse elements,
    iv. calculating at least one of the color, area, shape, texture, length/width ratio, and edge strength feature of each of said identified diverse elements of each of said multiple samples,
    v. classifying each of said calculated diverse elements for each of said multiple samples as one of leaf, pepper trash, bark, grass or shadow based on the calculated features of each of said elements for each of said multiple samples,
    vi. calculating percent area and count per inch$^2$ for each class of diverse elements for each of said multiple samples, vii. storing within said computer equipped with said artificial neural network the percent area and counts/in² associated with each classification of said diverse elements for each of said training samples and the respective grades of each of said multiple samples which have been assigned thereto by the at least one human for each of said diverse elements,
viii. combining said human grades and said image data to produce a trained response, and
ix. storing said trained response in said computer for subsequent analysis and outputting of an instrument grade for unknown samples;

c. analyzing an unknown sample of cotton, comprising repeating steps b-i through b-vi hereinabove;

d. employing said trained artificial neural network in said computer, comparing said percent area and count/in² determined from said digital image of said unknown sample for each class of diverse elements to the stored percent area and count/in² of said multiple samples and outputting a grade for each of said classes for said unknown sample.

14. A method for the analysis and assignment of a grade to a sample of cotton comprising the steps of
  a. providing a computer equipped with an artificial network,
  b. training said computer using multiple samples of cotton with known Human Classer grades,
  c. using said trained computer, analyzing a sample of cotton having an unknown grade, and,
  d. outputting at least one of leaf, bark, grass, and pepper trash grade for said sample of unknown grade.

* * * * *